(12) United States Patent
Almouzni et al.

(10) Patent No.: US 7,781,174 B2
(45) Date of Patent: Aug. 24, 2010

(54) PROLIFERATION MARKERS IN CLINICAL PRACTICE AND THEIR USE FOR CANCER PROGNOSIS OR DIAGNOSIS

(75) Inventors: Genevieve Almouzni, Neuilly/Seine (FR); Sophie E. Polo, Cambridge (GB); Stamatios E. Theocharis, Athènes (GR); Philippe Vielh, Paris (FR)

(73) Assignees: Institut Curie, Paris (FR); Centre National de la Recherche Scientifique (CNRS), Paris (FR); Universite Pierre et Marie Curie, Paris (FR)

( * ) Notice: Subject to any disclaimer, the term of this patent is extended or adjusted under 35 U.S.C. 154(b) by 0 days.

(21) Appl. No.: 11/510,612

(22) Filed: Aug. 28, 2006

(65) Prior Publication Data

US 2007/0077577 A1    Apr. 5, 2007

Related U.S. Application Data

(63) Continuation-in-part of application No. PCT/EP2005/002578, filed on Feb. 28, 2005.

(60) Provisional application No. 60/548,111, filed on Feb. 27, 2004.

(51) Int. Cl.
    *G01N 33/53* (2006.01)
(52) U.S. Cl. ...................................................... 435/7.1
(58) Field of Classification Search ........................ None
    See application file for complete search history.

(56) References Cited

U.S. PATENT DOCUMENTS 6,071,715 A      6/2000  Qian et al.
7,445,892 B2 *  11/2008  Owa et al. ..................... 435/6

FOREIGN PATENT DOCUMENTS

WO     WO 03/025138 A      3/2003
WO     WO 03/025138 A2 *   3/2003

OTHER PUBLICATIONS

Polo et al (Cancer Research, Apr. 2004, 64:2371-2381).*
Hoek and Stillman (PNAS, Oct. 2003, 100(21):12183-12188).*
Marheineke and Krude (The Journal of Biological Chemistry, Jun. 1998, 273(24):15279-15286).*
Krude et al (J. Cell Science, 1996, 109:309-318)).*
Stillman (PNAS, Oct. 2003, 100(21):12183-12188).*
Marheineke and Krude (The Journal of Biological Chemistry, Jun. 1998, 273(24):15279-15286).*
Tockman et al (Cancer Res., 1992, 52:2711s-2718s).*
Hoek and Stillman (PNAS, Oct. 2003, 100(21):12183-12188).*
Shirono et al (Blood, May 1999, 73(6):1664-1671).*
Kaufman et al (Cell, 1995, (81): 1105-1114).*
International Preliminary Report issued in corresponding PCT/EP2005/002578 on Aug. 30, 2006.
Polo SE, "Chromatin Assembly Factor-1, a Marker of Clinical Value to Distinguish Quiescent from Proliferating Cells" *Cancer Research*, Apr. 1, 2004, vol. 64, pp. 2371-2381.
Song et al., "Genes Encoding Pir5, Beclin 1, RbAp48 and Aldolase b are up or down-regulated in Human Primary Hepatocellular Carcinoma" *World Journal of Gastroenterology* Feb. 15, 2004 China, vol. 10, No. 4, pp. 509-513, The WJG Press.
Marheineke et al. "Nucleosome Assembly Activity and Intracellular Localization of Human CAF-1 Changes During the Cell Division Cycle" *Journal of Biological Chemistry*, vol. 273, No. 24, Jun. 12, 1998, pp. 15279-15286, The American Society for Biochemistry and Molecular Biology, Inc.
Polo et al., "Régulation de l'expression de CAF-1, facteur d'assemblage de la chromatine, et prolifération cellulaire," Abstract, Cinquìene Collque des 3R, Presqu'île de Giens, Jun. 2003, Front Page & Summary with English language translation of the relevant parts.
Polo et al., "Chromatin Assembly and Cell Proliferation: Regulation of CAF-1 Expression," Poster presented during the Symposium in Giens, Jun. 2003.
Almouzni, "Dynamique de la chromatine," published on line, Feb. 5, 2004, with English language translation of relevant parts.
Polo et al., "Regulation of CAF-1 expression, chromatin assembly factor and cell proliferation," Abstract, published on line on Apr. 18, 2003, with English translation.

* cited by examiner

*Primary Examiner*—Sean E Aeder
(74) *Attorney, Agent, or Firm*—Buchanan Ingersoll & Rooney, PC

(57) ABSTRACT

The invention relates to a method for assessing the proliferative state of cells in a human or non human biological sample, comprising using Chromatin Assembly Factor-1 (CAF-1 in short) subunits as proliferation markers.

Figure 6:
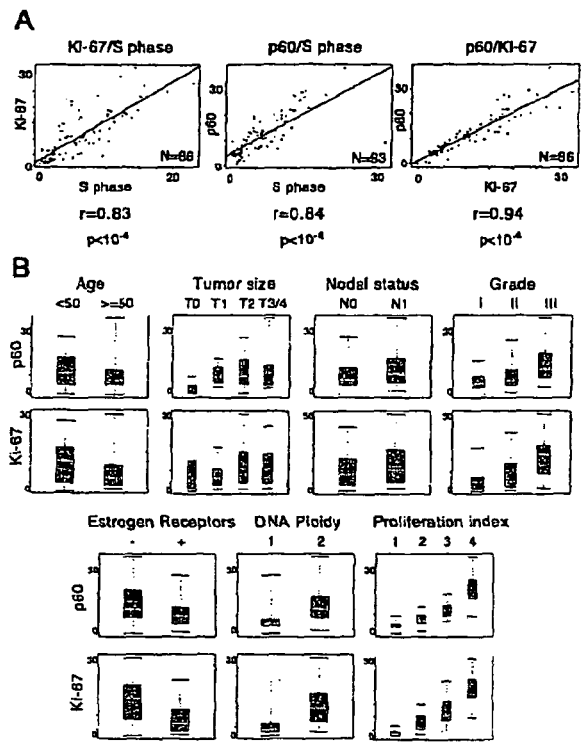

Application for cancer prognosis or diagnosis and monitoring tumor response in therapy.

15 Claims, 7 Drawing Sheets

Fig. 1
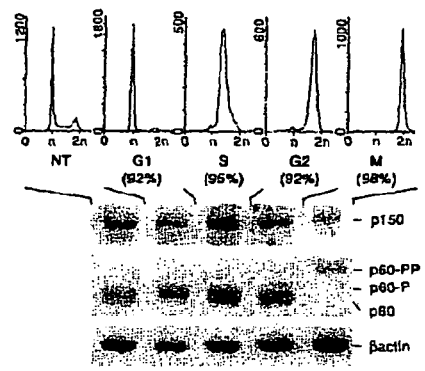
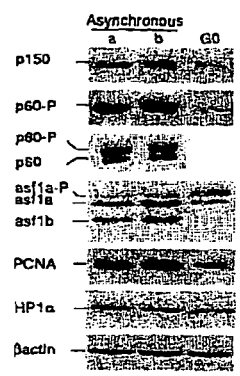
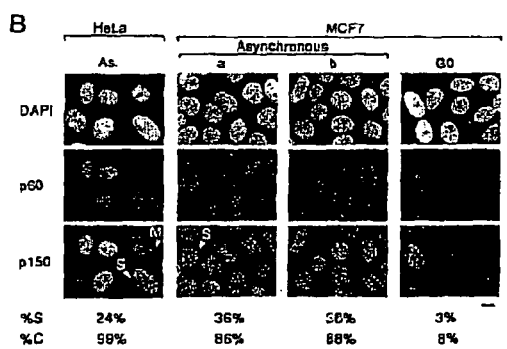
Fig. 2
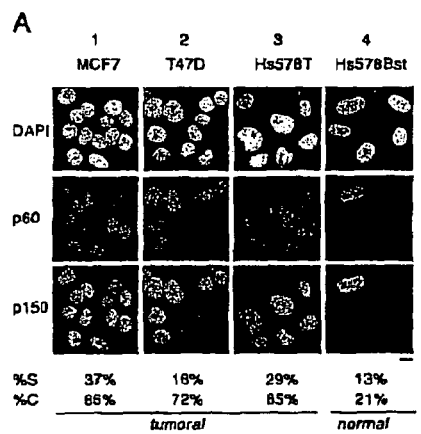
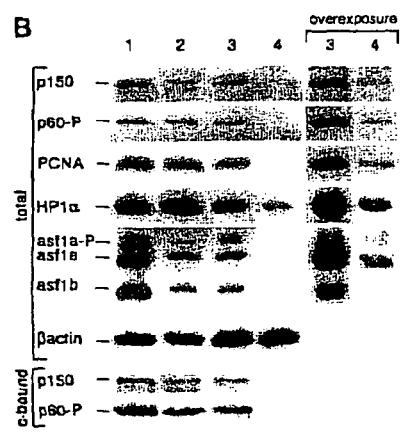

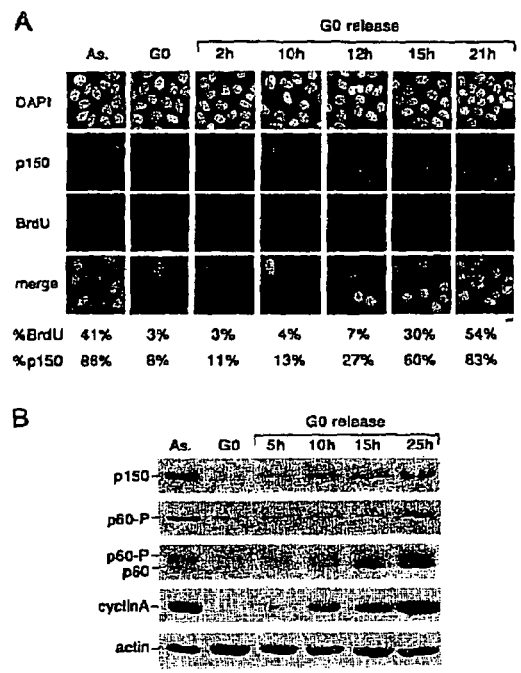
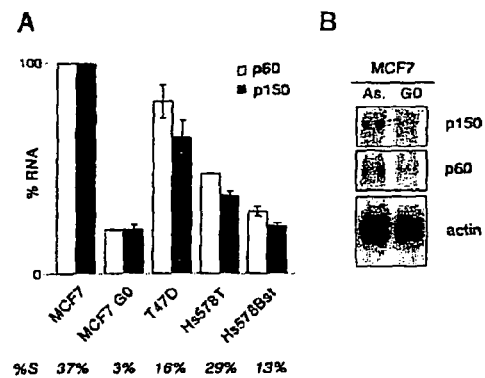
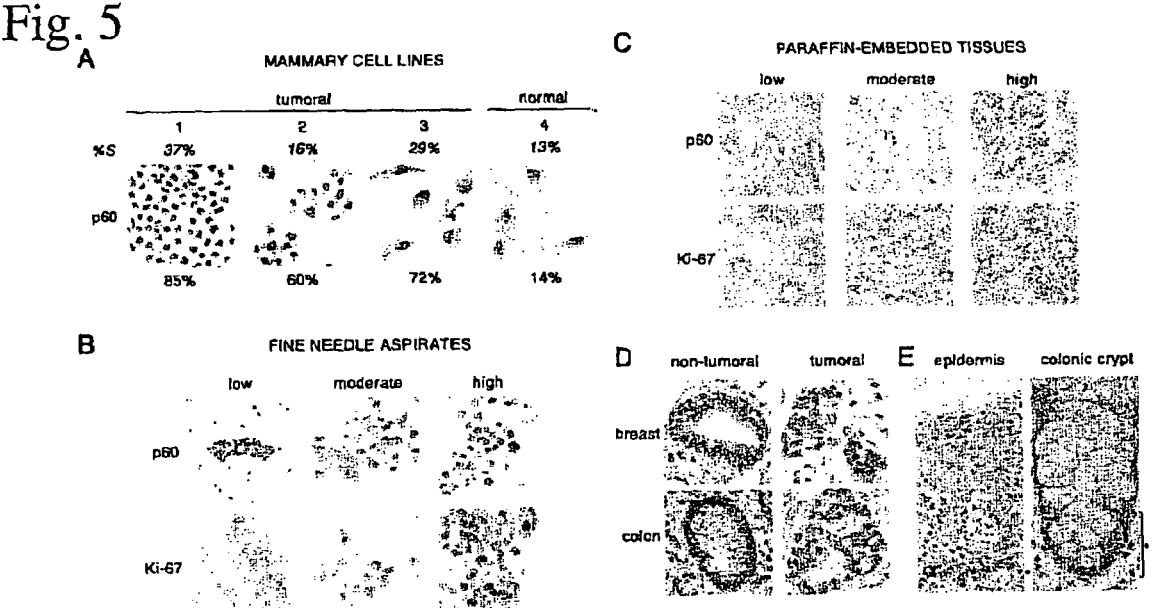

Fig. S1
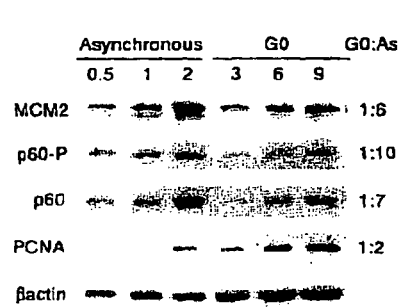
Fig. S2
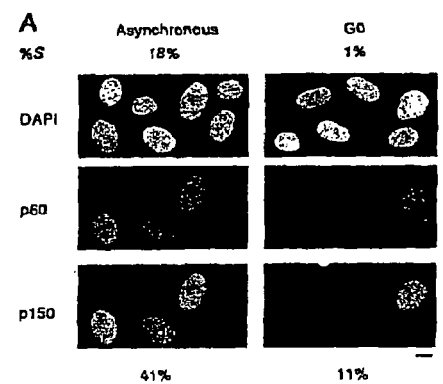
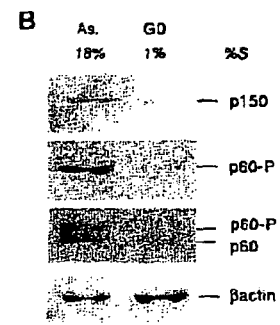
Fig. S3
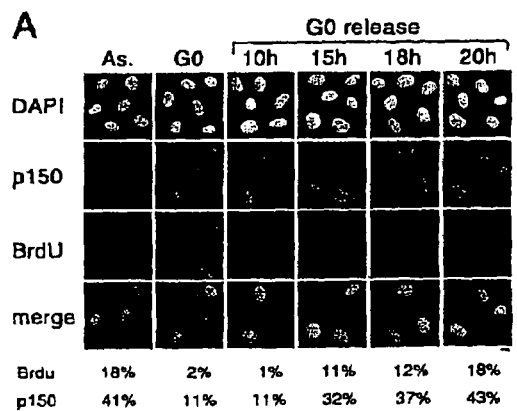

Fig. S4
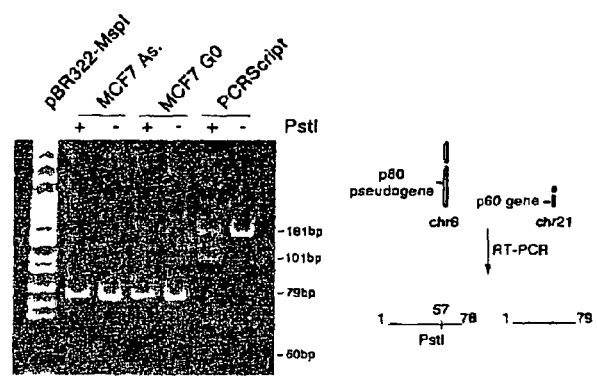
Fig. S5
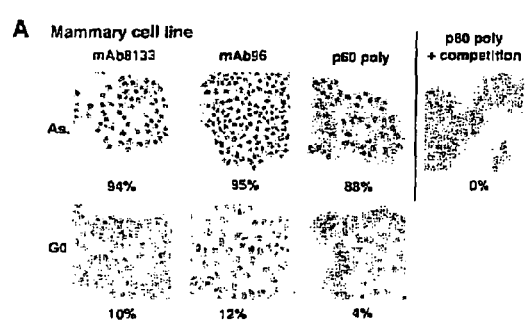
Fig. S6
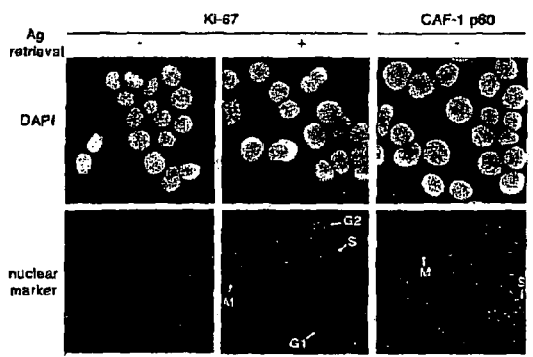
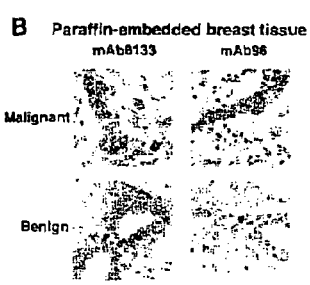

SEQUENCE LISTING

```
<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cggacactcc accaagttct                                             20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 2
ccaggcgtct ctgactgaat                                               20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggagcaggac agttggagtg                                               20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gacgaatggc tgagtacaga                                               20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cagcagtacc agtcccttcc                                               20

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tctttgcagt ctgagcttgt tc                                            22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggcgacctgg aagtccaact                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 8
ccatcagcac cacagccttc                                                 20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
accccgtgct gctgaccga                                                  19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcacagcctg gatagcaac                                                  19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggcacaaaga aaccatcgtc                                                 20
```

PROLIFERATION MARKERS IN CLINICAL PRACTICE AND THEIR USE FOR CANCER PROGNOSIS OR DIAGNOSIS

The invention relates to new proliferation markers in clinical practice and their use for cancer prognosis or diagnosis and monitoring tumour response in therapy.

In eukaryotic cells, nuclear DNA is compacted with proteins in the form of chromatin. During each cell cycle, DNA must be duplicated and the chromatin structure re-established, which requires a tight coordination with histone synthesis. Therefore, defects affecting any of these events are likely to impinge upon cell cycle progression. Histone deposition is particularly interesting in this context since it depends both on the availability of histones and on the assistance of auxiliary factors among which chaperones represent a family of proteins that have recently gained significant interest.

To gain insights into how certain assembly factors are controlled and whether they may represent physiologically relevant targets for cell cycle regulation, of interest for human health, the inventors have examined their expression as a function of cellular proliferation in both cultured cells and clinical samples. Specifically, the aim was to analyze differences between proliferating and quiescent cells.

The inventors particularly focused upon histone chaperones among which Chromatin Assembly Factor-1 (CAF-1 in short) comprising three subunits, and have found that this specific histone chaperone, was massively downregulated in quiescent cells compared to cycling populations, whereas the expression of the chromatin assembly factor HIRA remains constant.

In view of the results obtained by the inventors, it appears that said specific histone chaperone is a good indicator of the proliferate state.

Accordingly, it is an object of the invention to provide new markers and methods for assessing the proliferating state of cell populations, and kits for performing said methods.

Another object of the invention comprises the use of such markers, methods and kits in the context of cancer pathology.

The invention thus relates to a method for assessing the proliferative state of cells in a human or non human biological sample, comprising the use of proliferation markers selected in the group comprising the expression or the transcription products of CAF-1 sub-units.

CAF-1 is known for its ability to facilitate deposition of histones H3 and H4 on newly synthesized DNA. CAF-1 is a heterotrimeric complex comprising p150, p60 and p48 subunits. The p48 subunit is an escort protein which is part of several additional complexes that are involved in histone metabolism.

As shown in the examples, the transcription and translation products of CAF-1 gene were found to be a powerful marker of cell proliferation.

Upon exit from the quiescent state, CAF-1 subunits were detected early after cell cycle entry, prior to S phase. The total pool of CAF-1 was distinguished from the fraction tightly associated with chromatin, that is believed to correspond to the active molecules. The amount of CAF-1 proteins corresponding to each pool correlated directly with the proliferative state of the cells. This result supports a connection between the regulation of the amount of available CAF-1 in a cell and its usage at the chromatin level. Furthermore, the inventors found that CAF-1 expression appeared to be regulated largely at the RNA level, when comparisons were made based on the proliferative state.

According to an embodiment of the invention, said detection is carried out at the protein level.

The method of the invention thus comprises detecting CAF-1 p60 and p150 subunits, advantageously CAF-1 p60.

It also comprises detecting the phosphorylated derivatives thereof.

Alternatively, the method of the invention comprises detecting the total cellular fraction or the chromatin-bound fraction of CAF-1 subunits or phosphorylated derivatives thereof in the cell nucleus.

Advantageously, the detection methods at the protein level are for example performed by immunofluorescence, Western blot, with protein chips, and preferably by immunocytochemistry or immunohistochemistry.

Said methods are advantageously carried out by using the usual protocols known by the man skilled in the art.

The method for assessing the proliferation state of cells in a human or non human biological sample is then carried out with anti-CAF-1 antibodies, or antibodies targeted against individual CAF-1 subunits or against fragments thereof. Said antibodies are polyclonal or monoclonal antibodies.

The method is performed on cryosections, cytospined or smeared samples, on coverslips or slides or on paraffin-embedded tissues.

In another embodiment of the invention, the detection of CAF-1 p150 or p60 subunit is carried out at the RNA level In still another embodiment, CAF-1 p150 or p60 subunit expression is detected at the RNA level. As illustrated by the Examples, the inventors have shown that in human cell lines, CAF-1 p150 and p60 mRNA levels measured by quantitative RT-PCR can distinguish between tumoral and healthy cells and between quiescent and cycling cells, (see FIG. 10).

Examples of primers pairs comprise: p60-forward, CGGACACTCCACCAAGTTCT (SEQ ID NO: 1); p60-reverse, CCAGGCGTCTCTGACTGAAT (SEQ ID NO: 2); p150-forward, GGAGCAGGACAGTTGGAGTG (SEQ ID NO: 3); p150-reverse, GACGAATGGCTGAGTACAGA (SEQ ID NO: 4).

Advantageously, the detection methods at the RNA level are for example performed by quantitative or semi-quantitative PCR, Northern blot or RNA chips.

Said methods are advantageously carried out by using the usual protocols known by the man skilled in the art.

On patient samples, CAF-1 levels can be analyzed in a reliable manner in mRNA extractions from fine needle aspirates (and from cryopreserved tissue), provided that RNA degradation is minimal. For this, RNA extraction is performed in RNase free conditions and collected cells are ejected directly in a reagent such as Trizol (Invitrogen). Importantly, small amplicons (around 100 bp) are chosen for quantitative RT-PCR analysis in order to minimize the effect of degraded material on the final interpretation. Forward and reverse primers are chosen in different exons of the genes, in order to distinguish between amplification of cDNA and contaminating genomic DNA, based on the size of the amplicon. The reference gene, according to which results should be normalized, is the human acidic ribosomal phosphoprotein PO (RPLPO; also referred to as 36B4), a widely used control in quantitative RT-PCR since the gene seems to be under translational control.

The invention also relates to kits useful for assessing the proliferation state of cells in a human or non human biological sample.

For a detection at the protein level, said kits advantageously comprise a fixative solution for the biological sample to be tested and anti-CAF-1 p60 and/or CAF-1 p150 antibodies. Preferably, the kits of the invention also comprise a buffer and/or a blocking agent and/or a secondary antibody and/or reagents to prepare an avidin-biotin complex and/or a counter-staining solution.

For a detection at the RNA level, the kits of the invention advantageously comprise lyophilized forward and reverse primers for CAF-1 p60 and p150 and RPLPO, control consisting of vials of cDNA made from RNA extracts of cycling and quiescent primary cells.

The invention thus provides means for discriminating between proliferating and quiescent cells in human sample.

The invention particularly relates to the use of said methods in cancer diagnosis, prognosis or monitoring tumor response in therapy.

In certain types of cancer, the assessment of cellular proliferation is essential for the characterization of a tumor and also for survival prediction and patients' monitoring. At present, the only routinely used markers for assessing cellular proliferation in immunocyto- and histo-chemistry are Ki-67 and, to a lesser extent, PCNA. The assessment of MCM protein expression has recently been introduced as a novel proliferation marker.

The CAF-1 biomarker of the invention is particularly useful for assessing cellular proliferation in case of solid tumors such as breast, colon, gastric, renal, thyroid, prostate, endometrial and cervical cancers. CAF-1 offers a technical advantage over detection of for example Ki-67 since no antigen unmasking step is required on cytological specimens. This could allow speeding up the staining process and most importantly reducing staining variability.

Figure 7:
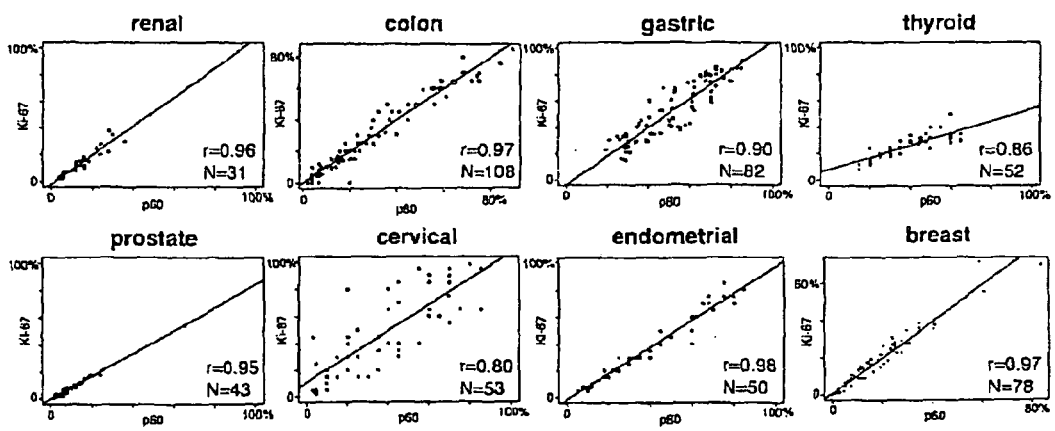
Figure 8:
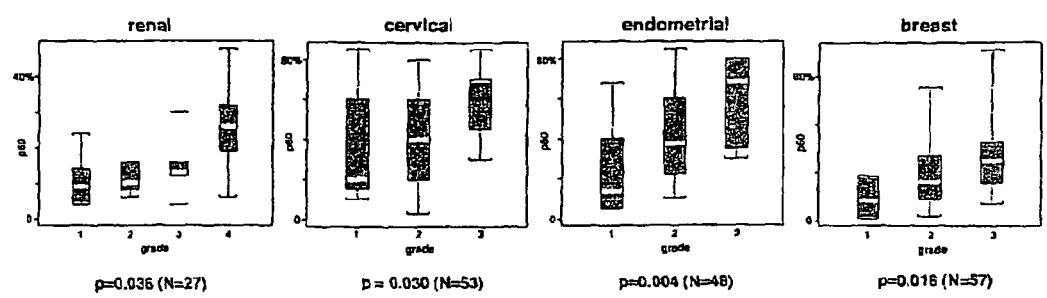
Figure 9:
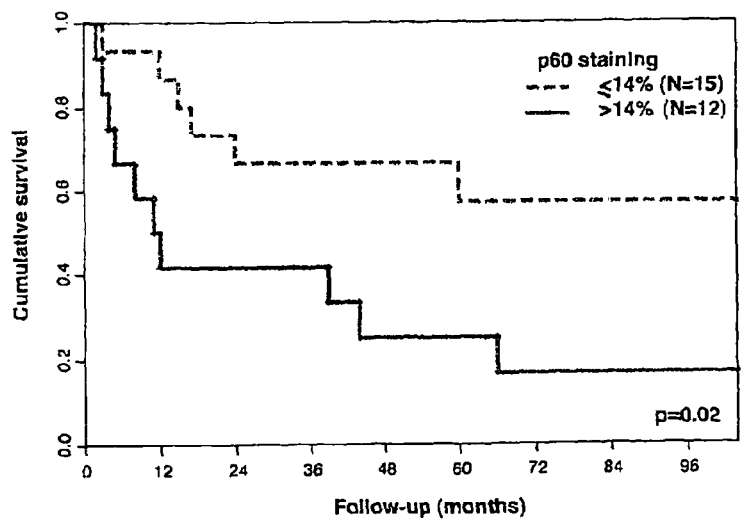

Other characteristics and advantages of the invention will be given hereinafter with reference to the figures which represent, respectively:

FIG. 1: G0 regulation of CAF-1 and its partners;

FIG. 2: Expression of CAF-1 subunits and its partners in human mammary cell lines;

FIG. 3: Expression of CAF-1 subunits upon G0 release in MCF7 cells;

FIG. 4: CAF-1 regulation at the RNA level. P60 and p150 RNA levels assessed by quantitative RT-PCR;

FIG. 5: Immunocyto- and histo-chemical detection of CAF-1 p60;

FIG. 6: Use of CAF-1 p60 as proliferation marker in human breast cancer;

FIG. 7: Graphical representation of the correlations between the percentages of CAF-1 p60 and Ki-67 positively stained cells;

FIG. 8: Boxplot representation of p60 value distributions according to histological grade;

FIG. 9: Kaplan-Meier survival analysis of patients with renal cancer.

Figure 10:
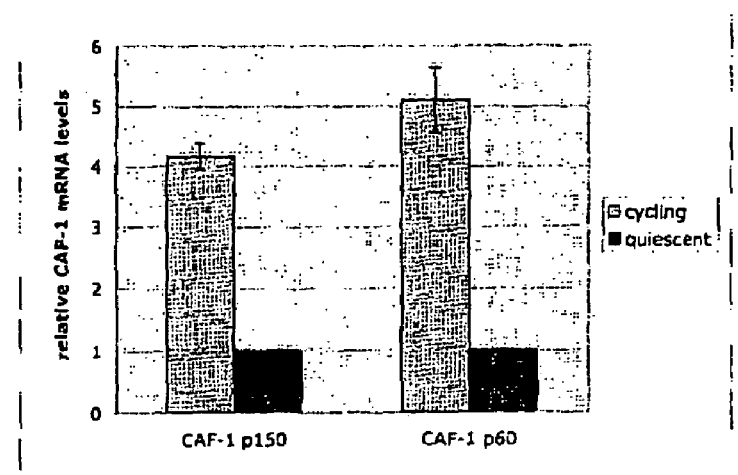

FIG. 10: Determination of CAF-1 p150 and p60 mRNA levels by quantitative RT-PCR, in cycling and serum-deprived (quiescent) primary BJ cells. Expression levels are normalized to RPLPO and levels in quiescent cells were set at 1.

Supplementary Data

FIG. S1: CAF-1 downregulation level in quiescent cells;

FIG. S2: CAF-1 expression in quiescent versus proliferating 1BR3 cells;

FIG. S3: Expression of CAF-1 upon G0 release in 1BR3 cells;

FIG. S4: Analysis of p60 pseudogene putative transcript;

FIG. S5: Specificity of immunocytochemical detection for CAF-1 p60;

FIG. S6: Ki-67 and CAF-1 immunodetection in MCF7 cells.

MATERIAL AND METHODS

Cell culture, Synchronization. HeLa cells MCF7, T47D and Hs578T mammary tumoral cells Hs578Bst mammary normal cells (LGC Promochem, Molsheim, France) and 1BR3 skin primary fibroblasts (were grown in Petri dishes (Falcon Plastics, Cockeysville, Md.) in the appropriate medium complemented with 10% fetal calf serum, 10 mg/ml antibiotics (penicillin and streptomycin) and 2 mM L-Glutamin (Invitrogen, Carlsbad, Calif.). HeLa and MCF7 cells were grown in DMEM (Dulbecco's Modified Eagle's Medium), T47D cells in RPMI, Hs578T cells in RPMI complemented with 10 mg/ml insulin (Invitrogen), Hs578Bst in DMEM complemented with 30 ng/ml Epidermal Growth Factor (EGF) (PeproTech, Rocky Hill, N.J.) and 1BR3 cells in MEM (Modified Eagle's Medium). Normal Hs578Bst cell line is derived from the same patient as Hs578T tumoral cell line.

HeLa cells were synchronized in G1, S and G2 by a double thymidine block: 25 h block in 2 mM thymidine (Sigma Aldrich, Lyon, France), 12 h release in 30 µM 2'-deoxycytidine (Sigma Aldrich), 25 h block in 2 mM thymidine followed by 3 h, 8 h and 14 h release in 30 µM 2'-deoxycytidine to collect S, G2 and G1 cells respectively. HeLa mitotic cells were obtained by mitotic shake-off after 19 h treatment with 10 ng/ml nocodazole (Sigma Aldrich). 1BR3 cells were blocked in G0 by 4 days serum starvation, MCF7 cells by 48 h treatment with 10 nM ICI 182780, an estrogen receptor antagonist (Fischer Bioblock Scientific, Ilkirch, France). 1BR3 cells were released from G0 by adding back serum in culture medium, MCF7 cells by treatment with 100 nM 17-bêta estradiol E2 (Sigma Aldrich). Synchronization analyses were performed by flow cytometry after propidium iodide intercalation (Sigma Aldrich). Percentages of replicating S-phase cells were determined by flow cytometry after BrdU incorporation (Sigma Aldrich).

Antibodies. Primary antibodies used were anti-p150 mAb7655 and anti-p60 mAb8133 (Abcam, Cambridge, UK), anti-p60 poly, anti-ASF1 (S. E. Polo, Cancer Research, 2004, 64:2371-2381) obtained using recombinant proteins produced at our laboratory (immunization from Agrobio, Villeny, France), anti-HP1alpha 2G9 (Euromedex, Mundolsheim, France), anti-HIRA, anti-Ki67 MIB1 (Dako, Carpinteria, Calif.), anti-PCNA PC10 (Dako), anti-MCM2 BM28 (BD Pharmingen, San Diego, Calif.), anti-BrdU (Harlan Sera-Lab, Loughborough, UK), anti-cdc6 sc-8341 (Santa Cruz Biotechnology, Santa Cruz, Calif.), anti-bêta actin AC15 (Sigma Aldrich). Anti-p60 mAb8133 only recognizes the phosphorylated forms of p60 whereas anti-p60 poly recognizes both phosphorylated and unphosphorylated forms. Secondary antibodies coupled to FITC or Texas red were purchased from Jackson ImmunoResearch Laboratories, West Grove, Pa.

Immunofluorescence. Immunofluorescence on paraformaldehyde fixed cells was performed as described using an epifluorescence microscope (model DMRHC; Leica, Deerfield, Ill.) equipped with a HBO100 mercury lamp (Osram, München, Germany), a CoolSnap FX camera (Roper Scientific, Duluth, Ga.) and Metamorph 4.6 software (Universal Imaging Co., Marlow, GB) for image acquisition. Images were processed using Adobe Photoshop 5.5 software (San Jose, Calif.). The percentages of positively stained cells were obtained by counting at least 500 cells in each case. BrdU immunodetection was performed as described.

Cell extracts, Western Blot. Nuclear, cytosolic, total and Triton cell extracts were prepared and subjected to Western Blotting as described Serial dilutions were loaded for each sample in order to check signal linearity. Protein amounts were estimated by Bradford analysis (for nuclear and cytosolic extracts), by detection of beta actin levels (for total extracts) or by Ponceau staining (for Triton cell extracts). Quantification was performed using Quantity One 4.2.1 software.

RNA extracts, Real Time Quantitative RT-PCR, Northern Blot. Total RNA was extracted using RNA NOW (Biogentex, Seabrook, Tex.) according to manufacturer's instructions. To avoid any contamination by genomic DNA, DNA was digested by DNAse1 RNAse free RQ1 (Promega, Madison, Wis.) for 30 min at 37° C. DNAse 1 was then inactivated by heating at 65° C. for 10 min.

A quantification of p150 and p60 RNA levels was performed relatively to beta actin RNA level as an internal control. Primers pairs (Sigma Genosys, Cambridge, UK) were designed using Oligo6 software: p60-forward, CGGA-CACTCCACCAAGTTCT (SEQ ID NO: 1); p60-reverse, CCAGGCGTCTCTGACTGAAT (SEQ ID NO: 2); p150-forward, GGAGCAGGACAGTTGGAGTG (SEQ ID NO: 3); p150-reverse, GACGAATGGCTGAGTACAGA (SEQ ID NO: 4); bêta actin-forward, ACCCCGTGCTGCTGACCGA (SEQ ID NO: 9); bêta actin-reverse, GCACAGCCTGGAT-AGCAAC (SEQ ID NO: 10). Total RNA extracts were used in independent RT reactions with the Omniscript RT Kit (QIAGEN, Santa Clarita, Calif.) using the corresponding reverse primers except for p150 RT in Hs578B st cell line requiring another reverse primer (GGCACAAAGAAAC-CATCGTC (SEQ ID NO: 11)) to increase amplification specificity. Quantitative amplifications were performed with the LightCycler Fast Start DNA Master SYBR Green I Kit (Roche Diagnostics, Basel, Switzerland) according to manufacturer's instructions during 45 cycles at an hybridization temperature of 60° C. Amplification efficiency was determined from serial 1/5 dilutions of the RT products. Considering every amplification 100% efficient, the relative amount of p150 or p60 RNA normalized to the internal control bêta actin was calculated as follows: $2^{-\Delta\Delta C_T}$ where $\Delta\Delta C_T=(C_{T\ target}-C_{T\ actin})_{sample}-(C_{T\ target}-C_{T\ actin})_{calibrator}$;

the target is p150 or p60, the calibrator is arbitrarily chosen as asynchronous MCF7 cells.

15 μg of each RNA sample were subjected to a Northern Blot analysis with the following modifications. RNA was transferred overnight to Hybond N+ membrane (Amersham Biosciences, Orsay, France) before UV crosslinking. Membrane hybridization was performed overnight at 60° C. in Rapid Hyb Buffer (Amersham Biosciences) containing the DNA probe. Human bêta actin cDNA control probe (1.8 kb) was purchased from BD Clontech (San Jose, Calif.), p150 and p60 cDNA probes (1.2 kb each) were obtained by double digestion of plasmids containing the corresponding full length cDNA (10) and purification of the digestion product from an agarose gel. Random probe labelling was carried out using Rediprime II kit (Amersham Biosciences) with [alpha-$^{32}$P]dCTP (50 μCi/25 ng of DNA probe) according to manufacturer's instructions. Detection was achieved using PhosphorImager STORM 860 (Molecular Dynamics, Sunnyvale, Calif.).

Patients and Specimens. 100 breast tumoral samples obtained from 98 patients were included in this study. Before diagnostic investigations, each patient had given informed consent. Patients' age ranged from 18 to 98 years (mean: 56.8 years). Tumors were nonpalpable (T0) in 8%, T1 in 17%, T2 in 49% and T3 and 4 in 26% of cases. 64 patients were node negative and 34 had palpable axillary lymphadenopathies. Fine needle aspirations were performed by pathologist at specialized consultation at the Institut Curie (Paris, France). Nonpalpable tumors were sampled using ultrasound-guided technique. Aspirates were smeared on two slides for diagnosis and on three other slides (Superfrost+) for immunocytochemical studies. Histologically, 8 tumors proved to be benign (fibroadenomas: 5; abscess: 2; tuberculoid granuloma: 1), and 92 malignant. Among malignancies, 1 was ductal in situ, 79 ductal infiltrative, 8 lobular infiltrative, and 4 belonged to other types of infiltrative malignancies. Carcinomas were graded as I in 13, II in 45 and III in 31 cases. 11 cases were non gradable. Estrogen receptors (ER) status was determined by immunohistochemistry on histological sections in 90 cases presenting positivity in 64 cases while 26 were negative.

DNA flow cytometry. All DNA flow cytometry analyses were performed on a FACScan flow cytometer (Becton Dickinson, San Jose, Calif.) equipped with a doublet discrimination module. Nuclear DNA content was measured by flow cytometry on cell suspensions obtained by fine-needle aspiration (FNA). Clinical samples were checked prior to analysis by light microscopy on cytocentrifuged preparations stained using the May-Grünwald-Giemsa procedure in order to verify that at least 80% of material was composed of tumoral nuclei. Data files from at least 10,000 nuclei stained using propidium iodide were acquired in list mode. Tumors with a DNA index ranging from 0.9 to 1.1 were classified as diploid; those with a single DNA index lower than 0.9 or over 1.1 were classified as aneuploid and the others were classified as multiploid. S phase fractions were computed using ModFit LT 2.0 software (Verity Software House, Topsham, Me.). Tumors were DNA diploid in 41 and DNA aneuploid/multiploid in 58 cases (in 1 case, ploidy could not be determined). S phase ranged from 0.3 to 31.4% (mean: 5.76%). S phase percentages were subdivided into 4 groups (proliferation indexes): very low (0-2%), low (2-4.5%), moderate (4.5-10%) and high (>10%), standard commonly used for clinical studies at the Curie Institute.

Immunocytochemistry, Immunohistochemistry. Immunostainings for p60, Ki-67 and PCNA were performed on paraformaldehyde fixed smears or on formalin-fixed paraffin embedded tissue sections (4 μm) using the appropriate antibody, a Vectastain Elite ABC-peroxidase kit (Vector Laboratories, Peterborough, UK) and the Liquid DAB Substrate-Chromogen System (Dako) according to manufacturer's instructions. For every antigen detection in paraffin embedded tissues and for Ki-67 detection in smears, an additional step of antigen retrieval (citrate buffer pH 6.1 and microwave heating) was performed before antibody incubation. Cells were counterstained with hematoxylin (Merck, Darmstadt, Germany).

Statistical analysis. The percentages of positively stained cells in immunocytochemistry experiments were obtained by counting at least 1000 cells in each case by two independent observers. Concordance between the two observers was demonstrated by calculating an intra-class correlation coefficient, allowing us to use the mean values for the following statistical analyses. Correlations were evaluated using the Spearman rank test. Average comparisons between multiple groups were determined by analysis of variances in case of homogeneous variances (according to the Bartlett test) or by the Kruskal-Wallis test. Statistical significance was taken as p<0.05. Overall survival was calculated from the date of tumor excision to the date of death or last follow-up. Survival curves were derived from Kaplan-Meier estimates and compared by log-rank test. Univariate Cox regressions were also carried out. Statistical significance was taken as p<0.05. Statistical analyses were performed using SPlus 2000 software.

Clinical Specimens. Archival formalin-fixed, paraffin-embedded tissues and clinical material of renal, colon, gastric, thyroid, prostate, cervical, endometrial and breast cancer cases were obtained from different Departments of the Medical School of the University of Athens, Greece (clinicopathological details are available in Table 1). Four µm tissue sections were subject to immunohistochemical staining for CAF-1 p60 (mAb8133, Abcam), Ki-67 (MIB1, DAKO) and MCM proteins (MCM-2: MCA1859; MCM-5:MCA1860, Serotec).

Results

In Quiescent Cells, the Expression Pattern of the Assembly Factors CAF-1, ASF1 and HIRA Revealed a Major Downregulation of CAF-1.

First, the expression of CAF-1 p150 and p60 subunits during the cell cycle was analyzed by Western Blot on whole-cell extracts derived from synchronized HeLa cells.

The results are given in FIG. 1: A, Western Blot analysis of CAF-1 p150 and p60 in total cell extracts from asynchronous (NT) and synchronized HeLa cells arrested in G1, S, G2 (double thymidine block) and M (nocodazole). In each case, a lysate corresponding to $10^5$ cells was loaded. βactin is used as loading control. The corresponding FACS profiles are shown above. B, Expression of CAF-1 p150 and p60 subunits revealed by immunofluorescence in HeLa and MCF7 cells. MCF7 cells are untreated (a), DMSO treated (b) or blocked in G0 with ICI 182780 10 nM in DMSO for 48 h (G0). S phase fractions (% S) and percentages of CAF-1 p150 and p60 stained cells (% C) are indicated below. Bar, 10 µm. C, Total cell extracts from untreated (a), DMSO treated (b) or G0 blocked MCF7 cells were used in semi-quantitative Western Blot to analyze the expression of CAF-1 subunits (p150, p60) and CAF-1 partners (ASF1, PCNA, HP1). For simplicity, several analyses with similar βactin levels (internal control) are juxtaposed. In each case, a lysate corresponding to $10^5$ cells was loaded. D, Upper Panel: HIRA, CAF-1 p150 and p60 (anti-p60 poly) expression analyzed by Western Blot in cytosolic and nuclear extracts from asynchronously proliferating (AS) or G0 blocked (G0) MCF7 cells. 10 µg of proteins were loaded in each case. Lower panel: HIRA and CAF-1 p60 (anti-p60 poly) expression analyzed by immunofluorescence in asynchronously proliferating (AS) or G0 blocked (G0) MCF7 cells. Bar, 10 µm.

As previously described, variations in p60 phosphorylation profile could be detected (FIG. 1A). CAF-1 p150 and p60 subunits appeared to be expressed essentially in comparable amounts at all stages of the cell cycle.

Experiments were then carried out to determine whether CAF-1 expression is maintained or not when cells exit from the cell cycle to enter quiescence.

In order to investigate CAF-1 expression in non-proliferating cells, p150 and p60 expression levels was compared by cellular immunodetection and semi-quantitative Western Blot in quiescent (G0) and asynchronously proliferating cells.

Tumoral MCF7 cells were arrested in G0 by ICI182780. G0 arrest was verified by flow cytometry: BrdU incorporation dropped from 36% to 3%. 93% of the cells were arrested in G0/G1 after treatment. G0 was distinguished from G1 by the reduced expression level of cdc6 (below the detection limits in Western Blot). Blocking efficiency was estimated at about 93%.

Immunofluorescence experiments revealed a nuclear location and colocalisation of CAF-1 p150 and p60 in MCF7 cells (FIG. 1B). The staining in these cells also displayed characteristic S phase profiles. Most importantly, a noticeable decrease in the number of cells expressing p150 and p60 was observed after G0 block. Indeed, the numbers gave a drop from 86% to 8% (FIG. 1B).

The lack of CAF-1 detection by immunofluorescence in G0 cells could be due to epitope masking or to a downregulation in protein expression.

In order to distinguish between these two possibilities, CAF-1 protein levels were examined by semi-quantitative Western Blot, with βactin as loading control. It was found that CAF-1 p150 and p60 expression is indeed downregulated in G0 cells (FIG. 1C). Both phosphorylated and unphosphorylated forms of p60 are affected in G0 (10-fold and 7-fold decrease, respectively) (supplementary FIG. S1 which gives expression of MCM2, CAF-1 p60 phosphorylated form (mAb8133), total CAF-1 p60 (anti-p60 poly) and PCNA analyzed in total cell extracts from asynchronous and G0 arrested MCF7 cells by semi-quantitative Western Blot with βactin as loading control. The downregulation level in quiescent cells is given in each case. Relative amounts of loaded extracts are indicated above).

Considering the massive downregulation of CAF-1 in quiescent cells, the regulation of some of its interacting partners was studied.

PCNA is the first-described partner of CAF-1 p150. The results obtained showed that PCNA is also downregulated in G0, consistent with its use as a proliferation marker, but to a lesser extent than CAF-1 (2-fold decrease) (FIG. 1C, supplementary FIG. S1). This may be due to a longer half-life of PCNA since lower PCNA levels can be detected in long-term quiescent cells.

The expression of ASF-1, a histone H3 and H4 chaperone that interacts and synergizes with CAF-1 during replication and repair was next examined. It was found that the expression of the ASF-1b isoform is substantially reduced in G0 compared to asynchronous cells. The total level of ASF1a is less affected, but ASF1a is hyperphosphorylated in G0. Indeed, the ratio of phosphorylated to unphosphorylated form shifts from 1:3 to 3:1 after G0 arrest (FIG. 1C).

In the case of HP1α, another p150 partner, no significant difference was found between quiescent and cycling cells (FIG. 1C).

Thus CAF-1 is regulated concordantly with several of its partners, but it still appears to be the most powerful marker for discrimination between proliferating and quiescent cells. CAF-1 downregulation in G0 was confirmed in another type of cell line, 1BR3 primary fibroblasts. The results are given in supplementary FIG. S2: A, Expression of CAF-1 p150 (mAb7655) and p60 (anti-p60 poly) subunits analyzed by immunofluorescence in 1BR3 cells grown with (asynchronous) or without serum (G0) during 4 days. Percentages of p150 and p60 stained cells are indicated below. Bar, 10 µm. B, Expression of CAF-1 subunits analyzed by semi-quantitative Western Blot in total cell extracts from asynchronous and G0 blocked 1BR3 cells. For simplicity, several analyses with similar βactin levels (internal control) are juxtaposed. In each case, a lysate corresponding to $10^5$ cells was loaded.

Said results show additionally that this regulation is not specific for immortalized and transformed cell lines but represents a more general phenomenon. This is consistent with the direct coupling of CAF-1 activity and DNA replication. Since quiescent cells do not replicate, they would not need CAF-1 to fulfill this particular function. However, renewal of histones may still be needed in long living resting cells and other factors should thus ensure deposition of histones.

One candidate for this function is the chromatin assembly factor HIRA. Indeed, it has been found to act independently from DNA synthesis in vitro with Xenopus egg extracts in contrast to CAF-1. It was thus interesting to compare HIRA expression to CAF-1 in quiescent cells. Remarkably, HIRA expression was not affected in G0 arrested MCF7 cells (FIG. 1D), suggesting that HIRA could ensure stability of chromatin in quiescent cells.

The amount of phosphorylated p60 appears to be a very good candidate for discriminating between cycling and resting cells.

Taken together, these results highlight the importance of the chromatin assembly factor CAF-1 as a major target for downregulation in quiescent cells. It is noteworthy that the downregulation level of the phosphorylated form of CAF-1 p60 in G0 is of greater magnitude than that of any of the other factors analyzed, including previously described proliferation markers, such as PCNA (2-fold decrease) and MCM2 (6-fold decrease) (supplementary FIG. S1).

The amounts of total and chromatin bound CAF-1 correlate directly with cell proliferation.

Experiments were carried out to study the expression of CAF-1 subunits and CAF-1 partners in various human mammary cell lines with different proliferation rates (estimated by BrdU incorporation): Hs578Bst normal cell line (13% in S phase), Hs578T, (providing a comparison between cells of similar origin) and T47D and MCF7 tumoral cell lines (29%, 16% and 37% in S phase, respectively).

The results are given in FIG. 2: 4 human epithelial mammary cell lines were studied: 3 tumoral MCF7 (1), T47D (2), Hs578T (3) and 1 normal Hs578Bst (4). A, Immunolocalization of CAF-1 p150 (mAb7655) and p60 (anti-p60 poly) in the indicated cell lines. Percentages of replicating cells determined by BrdU incorporation (% S) and percentages of CAF-1 p150 and p60 stained cells (% C) are indicated below. Bar, 10 µm. B, Cell extracts from the indicated cell lines were used in semi-quantitative Western Blot to analyze the expression of CAF-1 subunits (p150, p60) and CAF-1 partners (ASF1, PCNA, HP1). The amount of total and chromatin-bound (c-bound) proteins is determined from total and Triton-treated cell extracts respectively ($10^5$ and $25.10^4$ cells/well). Western Blot analyses with similar βactin levels or Ponceau staining (internal controls) are juxtaposed. An overexposure is provided to enable detection of signal in normal cells.

Immunofluorescence experiments (FIG. 2A) showed a higher percentage of cells expressing CAF-1 p150 and p60 in the tumoral cell lines (81% on average) versus the normal cell line (21%) and, among the tumoral cell lines, in MCF7 cells (86%) versus T47D cells, which proliferate more slowly (72%). Western Blot experiments indicated that CAF-1 subunits (p150, p60) as well as CAF-1 partners (ASF1a, ASF1b, PCNA, HP1α) are more abundantly expressed in tumoral versus normal cells (FIG. 2B). Only a higher exposure allowed detection of the signal in normal cells. Estimation of the relative levels of CAF-1 expression in these two cell types gave at least a 6-fold difference.

Taken together, these data show that the expression of CAF-1 and its partners correlates directly with cell proliferation.

As above-mentioned the chromatin-bound fraction of CAF-1 in the nucleus, distinguished from the soluble fraction on the basis of their resistance to detergent extraction is considered to be the CAF-1 active pool. This pool was found to be increased in tumoral cells as shown by Western Blot analysis (FIG. 2B). Although in normal cells the signal was below detection limit, we could clearly see a signal for the tumoral cell lines.

Said results show that the amount of active CAF-1 is directly related to CAF-1 total amount, i.e. availability, which is itself linked to the proliferative state of the cells.

CAF-1 Level Increases Upon G0 Release Before S Phase Entry.

Obviously, if CAF-1 decreases in G0, a need to produce it arises when cells re-enter the cell cycle. Experiments were then carried out to determine when CAF-1 proteins are re-expressed after G0 release and how this is related to cell cycle progression.

The results are given in FIG. 3: A, CAF-1 p150 expression (mAb7655) and BrdU incorporation analyzed by immunofluorescence in MCF7 cells at indicated times after G0 release compared to asynchronous (As.) and G0 arrested cells. Bar, 10 µm. B, Total extracts from MCF7 cells made at indicated times after G0 release analyzed by Western Blot ($10^5$ cells/well) in comparison with asynchronous (As.) and G0 arrested cells as indicated. βactin is used as loading control, cyclin A as S phase marker.

MCF7 cells were thus released from the quiescent phase and progression into the cell cycle was monitored. S phase entry occurred 12 h after G0 release as identified by an increase in the number of cells incorporating BrdU (FIG. 3A). As an additional marker of cell cycle progression into S phase, the increase in cyclin A expression after release was recorded (FIG. 3B). During G0 release, cells harboring distinct CAF-1 staining profiles typical of early, mid and late S phase could be identified. Consistent with a progression in S phase, accumulation of late S phase profiles was observed at the expense of early profiles as a function of time.

The number of cells staining positively for CAF-1 p150 and p60 increased after G0 release, as shown by immunofluorescence (FIG. 3A). This was confirmed semi-quantitatively by Western Blot analysis (FIG. 3B). Importantly, all S-phase cells identified by BrdU staining were consistently positive for CAF-1 staining although the converse was never observed (FIG. 3A). Similar results were obtained upon releasing 1BR3 primary fibroblasts from G0.

The results are given in supplementary FIG. S3: A, CAF-1 p150 expression and BrdU incorporation analyzed by immunofluorescence in 1BR3 cells at indicated times after G0 release compared to asynchronous (As.) and G0 arrested cells. Percentages of p150 and BrdU (S phase) stained cells are indicated below. Bar, 10 µm. B, Total extracts from 1BR3 cells made at indicated times after G0 release analyzed by Western Blot ($10^5$ cells/well) in comparison with asynchronous (As.) and G0 arrested cells as indicated. βactin is used as loading control.

Immunodetection of another marker of S phase, namely cyclin A, reinforced these previous observations.

CAF-1 subunits are then re-expressed upon G0 release before S phase entry, which is consistent with CAF-1 requirement during S phase for chromatin assembly coupled to DNA replication.

The Amount of CAF-1 RNA in a Cell Population Correlates with the Proliferative State.

The regulation of CAF-1 expression linked to cell proliferation could occur at the RNA (transcription activity, RNA stability) and/or at the protein (translation activity, protein stability) level. To examine CAF-1 regulation at the RNA level, p150 and p60 RNA levels were quantified in comparison with βactin RNA level by quantitative RT-PCR and Northern Blot analysis. The results are given in FIG. 4: (A) and Northern Blot (B) relative to βactin RNA in total RNA extracts from mammary cell lines. A, Graphical representation of quantitative RT-PCR results showing relative p60

(white) and p150 (black) RNA levels in the indicated cell lines. RNA levels are normalized to βactin transcripts. S phase fractions according to BrdU incorporation are indicated below. B, Northern Blot analysis of p60 and p150 RNA in asynchronously proliferating (As.) and G0 arrested (G0) MCF7 cells. The amount of βactin RNA was used as loading control.

Similar results were obtained from both experiments. The length of the amplicons from quantitative RT-PCR were as expected: 79 bp with p60 primers, 198 bp with p150 primers and 117 bp with βactin primers; amplification efficiencies were very close to each other and to 100%: 97% for p60 primers, 99% for p150 primers and 100% for βactin primers. For p60 RNA quantification, it was verified that the putative transcript arising from a p60 pseudogene on chromosome 6 was not affecting the results (supplementary FIG. S4: according to a BLAST search, the p60 gene is present in two copies in human genome: one on chromosome 21 and one pseudogene on chromosome 6 containing several point mutations. Of the two p60 RT-PCR products, the one from the putative pseudogene transcript comprises a PstI restriction site which is not present in the RT-PCR product from the p60 gene on chromosome 21 allowing discrimination between them. P60 specific RT-PCR reactions were performed on total RNA from proliferating and quiescent MCF7 cells. As a positive control, a fragment containing a PstI restriction site in PCR-Script plasmid (Stratagene) was amplified using KS and M13 primers (Sigma Genosys). PCR products were digested by PstI enzyme (Ozyme) and digestion products were analyzed on an 8% polyacrylamide gel).

Similar variations were found for both p150 and p60 RNA quantities between cell lines (FIG. 4A). Except for T47D cell line, in general these RNAs were less expressed in cells with low proliferation rates compared to rapidly proliferating MCF7. There was a five-fold increase in the amount of p150 and p60 RNA when comparing G0 arrested to asynchronously proliferating MCF7 cells (FIG. 4A, B).

Remarkably, this difference corresponds almost exactly to the one previously observed at the protein level (7-fold increase) (supplementary FIG. S1), demonstrating that a control at the RNA level could be sufficient to account for CAF-1 expression linked to the proliferative state in this particular cell type.

This correspondence is not observed for Hs578T versus Hs578Bst cells. In this case, a higher increase was observed in protein levels (at least 6-fold) (FIG. 2B) compared to RNA levels (about 1.5 fold) (FIG. 4A). Interestingly, this suggests that additional regulation at the protein level can also operate in these cells, which may relate to the existence of PEST domains in p150 and p60 subunits.

CAF-1 p60: a Proliferation Marker in Clinical Practice.

Immunocytochemistry is routinely used for clinical purposes since this technique offers two major advantages in comparison with immunofluorescence: correlation with cell morphology and the possibility to archive slides for reassessment.

Immunocytochemical staining for CAF-1 p60 was first carried out on mammary cell lines.

The results are given in FIG. 5: A, Immunocytochemical detection of phosphorylated p60 (mAb8133) in 4 epithelial mammary cell lines, 3 tumoral MCF7 (1), T47D (2), Hs578T (3) and 1 normal Hs578Bst (4), compared with the percentage of replicating S-phase cells. Percentages of p60 stained cells obtained by counting at least 1000 cells for each cell line are indicated below. Magnification is 400×. B, Immunocytochemical detection of Ki-67 and phosphorylated p60 (mAb8133) on fine needle aspirates from benign (low expression) and malignant breast lesions (moderate and high expression). Magnification is 400×. C, Immunohistochemical detection of Ki-67 and phosphorylated p60 (mAb8133) in paraffin-embedded tissues from benign (low expression) and malignant breast lesions (moderate and high expression). Magnification is 200×. D, Immunohistochemical detection of phosphorylated p60 (mAb8133) in paraffin-embedded tissues from breast and colon to compare tumoral and non-tumoral tissues. Magnification is 400×. E, Immunohistochemical detection of phosphorylated p60 (mAb8133) in paraffin-embedded tissues from normal skin (200×) and normal colon (400×). P60 expression in normal skin is restricted to the nuclei of basal and parabasal cells (*). P60 expression in normal colon is restricted to the lower third of colonic crypts (*).

The percentages of positively stained cells obtained by this technique (FIG. 5A) were consistent with the previous immunofluorescence experiments (FIG. 2A) but actually discriminated even more clearly between the different cell lines. The specificity of immunocytochemical detection for CAF-1 p60 was verified first by using different antibodies against p60 (monoclonal, polyclonal) and second by competition with a recombinant p60 protein.

The results are given in supplementary FIG. S5: A, Expression of p60 detected by immunocytochemistry on asynchronous (As.) and G0 arrested MCF7 cells using two distinct p60 monoclonal antibodies (mAb8133 from Abcam, mAb96 kindly provided by B. Stillman) and a polyclonal antibody (p60 poly) obtained using a recombinant His-p60 protein produced at our laboratory for rabbit immunization (Agrobio, Villeny, France). For competition experiment, we pre-incubated the p60 polyclonal antibody with a recombinant GST-p60 protein prior to immunostaining, which led to the disappearance of nuclear staining. Percentages of positively stained nuclei indicated below were reproducible throughout all experiments using different antibodies. Magnification is 200×.

B, Comparison of the expression of p60 detected by immunohistochemistry in malignant (high expression) and benign lesions (low expression) using paraffin-embedded breast tissue sections. Antibodies are as indicated. Magnification is 400×.

Consistent results were obtained when using the different sources of antibodies.

Preliminary results from immunocytochemical staining on cytology smears showed a good correlation between p60 and PCNA expression (r=0.95, p=0.0001) in a small number of cases (eighteen). However, since the use of PCNA as a proliferation marker has limitations due to antigen sensitivity to fixation time, further experiments were performed on a larger number of samples in comparison with the established proliferation marker Ki-67, which is widely used in routines for cancer diagnosis and prognosis. Immunocytochemical staining of CAF-1 p60 and Ki-67 were performed on cytology smears and on paraffin-embedded tissues, showing that CAF-1 p60 antibody can be used successfully on different types of clinical material (FIG. 5B, C). Additionally, the antibody against CAF-1 p60 allowed to detect proliferating cells within benign breast lesions (FIGS. 5B, C). It also discriminates clearly between non tumoral and tumoral tissues, the latter showing enhanced positivity (FIG. 5D). In normal tissues, proliferating cells found in the basal layer of skin epithelium and in the lower third of colonic crypts (FIG. 5E) are positively stained with our antibody.

In view of said data further experiments were performed to examine whether this antibody could be used as a clinical tool to mark proliferating cells.

p60 was then compared to the Ki-67 marker by counting positively stained cells on cytology smears.

The results are given in FIG. 6: All statistical analyses were done on data obtained from immunostaining on fine needle aspirates of breast tissue. A, Graphical representation of the correlations (Spearman test) between S phase fraction, the percentages of p60 and Ki-67 positively stained cells. N: number of cases; r: correlation factor. B, Boxplot representation of p60 (upper) and Ki-67 values distributions (lower) according to the indicated prognostic factors. The gray box corresponds to the 25th-75th percentile. Brackets: range; black point: mean; white line: median. DNA ploidy: diploid (1), aneuploid/multiploid (2); Proliferation index: very low (1), low (2), moderate (3), high (4).

The percentages obtained were concordant between two independent observers (intra-class correlation coefficient: 0.9981 for Ki-67 and 0.9983 for p60) so the mean percentages were used for statistical analyses. A significant correlation factor was achieved between p60 and Ki-67 expression ($r=0.94$, $p<10^4$) showing that p60 expression is a good indicator of cell proliferation (FIG. 6A). The correlation level is lower with S-phase, though still significant ($r=0.83$ with Ki-67 and $r=0.84$ with p60, $p<10^{-4}$) (FIG. 6A). This may be due to the fact that the procedures used were different (flow cytometry versus immunocytochemistry) and that Ki-67 and p60 are cell cycle (not only S-phase) markers. Finally, the correlations between CAF-1 p60 expression and several clinicopathological prognosis factors of practical use were examined (table 1, FIG. 6B).

P60 and Ki-67 values were obtained from immunocytochemistry on fine needle aspirates of breast tumors. P60 and Ki-67 average percentages are indicated for each group. Significative p-values are highlighted in bold. Proliferation indexes are classified according to the level of S-phase fraction as described in Material and Methods. N: number of cases.

Whereas no significant association was noted with age and lymph node status, a clear association was found for: tumor size ($p=0.0081$), grade ($p=0.0004$), estrogen receptor status ($p=0.019$), proliferation index ($p<0.0001$) and DNA ploidy ($p<0.0001$).

These results show a strong correlation between CAF-1 detection and proliferation state in tumors on a range of clinical samples derived from breast cancer, reinforcing the conclusions drawn with cultured cells.

CAF-1 appears then to be useful as a proliferation marker in clinical practice for breast cancer.

Diagnostic and Prognostic Value of CAF-1 in Solid Tumors

Based on a strong positive correlation with Ki-67 staining, CAF-1 has also been validated as a new proliferation marker in colon, gastric, renal, thyroid, prostate, endometrial and cervical cancers. FIG. 7 gives the graphical representation of the correlations between the percentages of CAF-1 p60 and Ki-67 positively stained 16: r=correlation coefficient (Spearman rank test); N=number of cases; All p values are $<10^{-4}$.

In table 2 are given the clinicopathological details of tumors studies (T: tumor size. N: lymph node invasion. M: metastases.)

TABLE 1

Average comparison of p60 and Ki-67 between multiple groups of prognostic factors.

| Clinico-pathological factors | p60 | | | Ki-67 | | |
|---|---|---|---|---|---|---|
| | N | % positivity | p-value | N | % positivity | p-value |
| Age | | | 0.062 | | | 0.0398 |
| <50 | 39 | 12.49 | | 32 | 12.86 | |
| >=50 | 61 | 9.57 | | 53 | 9.46 | |
| Tumor size | | | 0.0081 | | | 0.344 |
| T0 | 8 | 3.26 | | 3 | 6.02 | |
| T1 | 17 | 9.79 | | 16 | 8.52 | |
| T2 | 49 | 10.67 | | 41 | 11.6 | |
| T3, T4 | 26 | 12.61 | | 25 | 11.32 | |
| Nodal status | | | 0.075 | | | 0.105 |
| N0 | 65 | 9.71 | | 57 | 9.83 | |
| N1 | 35 | 12.56 | | 28 | 12.6 | |
| Grade | | | 0.0004 | | | 0.0002 |
| I | 13 | 6.84 | | 12 | 6.66 | |
| II | 45 | 9.86 | | 40 | 9.14 | |
| III | 31 | 15.14 | | 27 | 15.63 | |
| Estrogen receptor | | | 0.019 | | | 0.002 |
| negative | 26 | 14.91 | | 23 | 15.79 | |
| positive | 64 | 10.03 | | 57 | 9.16 | |
| Proliferation index | | | <10e-4 | | | <10e-4 |
| very low | 23 | 4.3 | | 20 | 3.8 | |
| low | 21 | 7.2 | | 18 | 7.35 | |
| moderate | 28 | 12.04 | | 24 | 11.62 | |
| high | 21 | 21.33 | | 20 | 19.97 | |
| DNA ploidy | | | <10e-4 | | | <10e-4 |
| Diploid | 41 | 6.74 | | 33 | 6.78 | |
| Aneuploid/multiploid | 58 | 13.51 | | 51 | 13.36 | |

| RENAL | | |
|---|---|---|
| Age | 57.4 | (33-73) |
| | N | % |
| Sex | 31 | |
| Female | 10 | 32 |
| Male | 21 | 68 |
| TNM | 31 | |
| T1, T2N0 | 6 | 19 |
| T2N+ | 2 | 6 |
| T3N0 | 13 | 42 |
| T3N+ | 3 | 10 |
| T4Nany | 7 | 23 |
| Histological type | 28 | |
| clear cell | 19 | 68 |
| papillary | 6 | 21 |
| chromophobe | 3 | 11 |
| sarcomatoid | 0 | 0 |
| Fuhrman grade | 27 | |
| I | 6 | 22 |
| II | 7 | 26 |
| III | 6 | 22 |
| IV | 8 | 30 |
| Status | 27 | |
| Dead | 16 | 59 |
| Alive | 11 | 41 |

| BREAST | | |
|---|---|---|
| Age | 54.9 | (22-88) |
| | N | % |
| Histological type | 80 | |
| ductal | 55 | 69 |
| lobular | 0 | 0 |
| mixed | 3 | 4 |
| fibroadenoma | 6 | 7 |
| fibrocystic disease | 16 | 20 |

-continued

|  |  |  |
|---|---:|---:|
| Histological grade | 57 |  |
| I | 7 | 12 |
| II | 34 | 60 |
| III | 16 | 28 |
| T | 57 |  |
| T1 | 23 | 40 |
| T2 | 26 | 46 |
| T3, T4 | 8 | 14 |
| N | 58 |  |
| N0 | 23 | 40 |
| N1 | 25 | 43 |
| N2 | 9 | 15 |
| N3 | 1 | 2 |
| M | 58 |  |
| M0 | 56 | 97 |
| M1 | 2 | 3 |

COLON

| | | |
|---|---:|---:|
| Age | 69.4 | (34-94) |
|  | N | % |

|  |  |  |
|---|---:|---:|
| Sex | 108 |  |
| Female | 44 | 41 |
| Male | 64 | 59 |
| Stage | 108 |  |
| A | 20 | 19 |
| B | 47 | 43 |
| C1 | 21 | 19 |
| C2 | 20 | 19 |
| Grade | 104 |  |
| I | 10 | 10 |
| II | 79 | 76 |
| III | 15 | 14 |
| Vessel invasion | 108 |  |
| Yes | 67 | 62 |
| No | 41 | 38 |

CERVICAL

| | | |
|---|---:|---:|
| Age | 52.8 | (30-91) |
|  | N | % |

|  |  |  |
|---|---:|---:|
| Histological type | 53 |  |
| adenocarcinoma | 9 | 17 |
| squamous | 37 | 70 |
| mixed type | 7 |  |
| Histological grade | 53 |  |
| well differentiated | 9 | 18 |
| moderately | 33 | 64 |
| poorly | 9 | 18 |
| FIGO stage | 51 |  |
| 1a1 | 1 | 2 |
| 1a2 | 4 | 8 |
| 1b1 | 42 | 82 |
| 1b2 | 3 | 6 |
| 2a | 1 | 2 |
| Lymph node invas. | 53 |  |
| Yes | 8 | 15 |
| No | 45 | 85 |
| Lymphatics invas. | 52 |  |
| Yes | 36 | 69 |
| No | 16 | 31 |
| Vessel invasion | 52 |  |
| Yes | 18 | 35 |
| No | 34 | 65 |
| Status | 30 |  |
| Dead | 8 | 27 |
| Alive | 22 | 73 |

-continued

GASTRIC

| | | |
|---|---:|---:|
| Age | 66.9 | (39-88) |
|  | N | % |

|  |  |  |
|---|---:|---:|
| Sex | 82 |  |
| Female | 24 | 29 |
| Male | 58 | 71 |
| T | 79 |  |
| T1 | 10 | 13 |
| T2 | 25 | 31 |
| T3 | 37 | 47 |
| T4 | 7 | 9 |
| N | 78 |  |
| N0 | 28 | 36 |
| N1 | 44 | 56 |
| N2 | 6 | 8 |
| M | 75 |  |
| M0 | 64 | 85 |
| M1 | 11 | 15 |
| Stage | 74 |  |
| 1a | 6 | 8 |
| 1b | 12 | 16 |
| 2 | 25 | 34 |
| 3a | 14 | 19 |
| 3b | 3 | 4 |
| 4 | 14 | 19 |
| Histological type | 81 |  |
| Intestinal | 40 | 49 |
| Diffuse | 36 | 45 |
| Mixed | 5 | 6 |
| Histological grade | 79 |  |
| well differentiated | 38 | 48 |
| moderately | 37 | 47 |
| poorly | 4 | 5 |
| Chemotherapy | 76 |  |
| No | 48 | 63 |
| Yes | 28 | 37 |

PROSTATE

| | | |
|---|---:|---:|
| Age | 68.6 | (59-79) |
|  | N | % |

|  |  |  |
|---|---:|---:|
| Gleason's score | 43 |  |
| 5 | 7 | 16 |
| 6 | 6 | 14 |
| 7 | 21 | 49 |
| 8 | 5 | 12 |
| 9 | 4 | 9 |
| T | 43 |  |
| 1 | 3 | 7 |
| 2 | 16 | 37 |
| 3 | 23 | 54 |
| 4 | 1 | 2 |

THYROID

| | | |
|---|---:|---:|
| Age | 44.8 | (14-78) |
|  | N | % |

|  |  |  |
|---|---:|---:|
| Sex | 52 |  |
| Female | 38 | 73 |
| Male | 14 | 27 |
| T | 50 |  |
| T1 | 5 | 10 |
| T2 | 23 | 46 |
| T3 | 11 | 22 |
| T4 | 11 | 22 |
| N | 50 |  |
| N0 | 23 | 46 |
| N1 | 27 | 54 |
| M | 50 |  |
| M0 | 47 | 94 |
| M1 | 3 | 6 |
| Stage | 52 |  |
| I | 11 | 21 |
| II | 15 | 29 |
| III | 21 | 40 |

-continued

| | | |
|---|---|---|
| IV | 5 | 10 |
| Histological type | 52 | |
| Myeloid | 35 | 67 |
| Huertle cell | 3 | 6 |
| Anaplastic | 2 | 4 |
| Papillary | 12 | 23 |
| Status | 52 | |
| Dead | 6 | 12 |
| Alive | 46 | 88 |

ENDOMETRIAL

| | | |
|---|---|---|
| Age | 63.7 | (40-82) |
| | N | % |
| Histological type | 50 | |
| adenocarcinoma | 40 | 80 |
| +squamous elt | 10 | 20 |
| Histological grade | 48 | |
| well differentiated | 14 | 29 |
| moderately | 28 | 58 |
| poorly | 6 | 13 |
| FIGO stage | 50 | |
| 1a | 5 | 10 |
| 1b | 18 | 36 |
| 1c | 19 | 38 |
| 2a | 3 | 6 |
| 2b | 1 | 2 |
| 3a | 2 | 4 |
| 4a | 2 | 2 |
| Status | 33 | |
| Dead | 3 | 9 |
| Alive | 30 | 91 |

Comparison of CAF-1 and MCM stainings was achieved choosing antibodies against MCM2 and MCM5 proteins which have been used in most studies. The results are given in table 3: Upper Correlations between the percentages of CAF-1 p60, MCM2 or MCM5 and Ki-67 positively stained cells in colon, gastric and thyroid cancers (Spearman rank test). N=number of cases; All p values are <$10^{-4}$. Lower Distribution of CAF-1 p60, Ki-67 and MCM values (%) in gastric and colon cancers.

TABLE 3

| | colon (N = 108) | gastric (N = 82) | thyroid (N = 52) |
|---|---|---|---|
| p60/MCM2 | nd | 0.65 | nd |
| p60/MCM5 | 0.79 (N = 45) | 0.44 | 0.81 |
| p60/Ki-67 | 0.97 | 0.90 | 0.86 |

| | median | min | max |
|---|---|---|---|
| gastric | | | |
| CAF-1 p60 | 52.5 | 19.5 | 85 |
| Ki-67 | 52.5 | 15 | 90 |
| MCM2 | 60 | 25 | 94.5 |
| MCM5 | 70 | 25.5 | 95.5 |
| colon | | | |
| CAF-1 p60 | 20 | 2 | 84 |
| Ki-67 | 20 | 2 | 76 |
| MCM5 | 45 | 18 | 91 |

Correlation between CAF-1 and MCM makers is significant yet not as strong as between CAF-1 and Ki-67 (Table 3). Notably, the distribution of MCM staining percentages is commonly shifted towards higher values compared to CAF-1 as observed in gastric and colon cancers (Table 3). CAF-1 can thus potentially be viewed as a more discriminative marker than MCM proteins.

Additionally, a significant association was found between CAF-1 staining and histological grade in renal, cervical, endometrial and breast cancers (FIG. 8: (Fuhrman for renal cancer; well (1), moderately (2) and poorly differentiated (3) for cervical, endometrial and breast cancers). The gray box corresponds to the 25th-75th percentile. Brackets: range; white line: median). Given the strong association that we already found on breast cytological specimens between CAF-1 staining and two prognostic factors namely proliferation index and grade (Polo et al, Cancer Res, 64, 2371-2381, 2004), the potential value of CAF-1 p60 in predicting clinical outcome was also investigated. CAF-1 p60 staining was significantly associated with overall survival in renal cancer (p=0.02) using a cut-off value of 14% (median) (FIG. 9: two clusters of patients are defined on the basis of the median of p60 percentages (i.e. 14%). P value is calculated using the log-rank test). There were 40% deaths in patients with p60 staining of less than 14% (mean survival 56 months; range 3-144 months) and 83% deaths in patients with p60 staining greater than 14% (mean survival 12 months; range 2-140 months). Univariate Cox regression analysis on CAF-1 p60 values dichotomized at 14% shows that a high p60 staining is strongly associated with poor outcome in this tumor type with a hazard ratio for death of 3.13 [1.13-8.66], p=0.028.

Said data highlight a striking correlation between CAF-1 expression and the proliferative state of cells, with a noticeable decrease in quiescent cells. This observation made in cell line models was further confirmed under physiological conditions on breast, colon, gastric, renal, thyroid, prostate, endometrial and cervical cancer samples. CAF-1 subunits appear then to be a relevant proliferation marker in these tumor types. Furthermore, said results show that CAF-1 expression linked to the proliferative state is controlled mainly at the RNA level.

These results have to be considered in the light of the current knowledge of CAF-1 function. Based mainly on in vitro studies, CAF-1 has been shown to be involved in chromatin assembly coupled to DNA synthesis during replication and repair. Replication is characteristic of S-phase whereas repair might occur in other phases as well as S phase. The correlation of CAF-1 expression and cell proliferation is coherent with the S-phase function and reinforces the link with DNA replication. However, CAF-1 is also expressed outside S phase in G1 and G2 (FIG. 1A), which could account for the function of CAF-1 associated with DNA repair. In the case of quiescent cells, which do not replicate DNA but in principle should also be able to undergo DNA repair, CAF-1 involvement in this process can be questioned. In this context, one can envision either that in G0 (i) the low amounts of CAF-1 may still be sufficient to ensure chromatin assembly coupled to DNA repair, alternatively (ii) another chromatin assembly factor, yet to be identified, may substitute for CAF-1. Considering that CAF-1 promotes chromatin assembly on newly synthesized DNA, its main requirement during DNA replication would thus be associated with the elongation process. However, based on our results, it is tempting to hypothesize that CAF-1 might also be involved at the initiation step of DNA replication. Indeed, we found that CAF-1 re-expression after release from the quiescent state occurs early prior to replication (FIG. 3) in parallel with MCM proteins known to be involved in the initiation of DNA replication.

Compared with other factors involved in chromatin assembly, CAF-1 appears as the most powerful discriminator between the proliferative and quiescent states. Indeed, contrary to CAF-1, the chromatin assembly factor HIRA is expressed at similar levels in both states (FIG. 1D) and thus cannot be used as a proliferation marker. Concerning ASF1, the ASF1b isoform only is massively downregulated in quiescent cells. At this time, distinction between the two ASF1 isoforms can be done in Western Blot and awaits further investigations in immunocyto- or histo-chemistry.

The inventors have also demonstrated that CAF-1 expression linked to the proliferative state is controlled at least in part at the RNA level (FIG. 2B and FIG. 4), offering a possibility to assess cell proliferation by examining CAF-1 RNA level. It should stress however that assessment at the protein level proved to be more reliable in all cell lines tested. The results showing a downregulation of CAF-1 at the RNA level in quiescent versus cycling cells supplement the current knowledge about the transcriptional regulation of CAF-1 during the cell cycle. Indeed, microarray analyses in human cells (HeLa cells and primary fibroblasts) showed that CAF-1 p150 and p60 RNA expression is cell cycle regulated with an increase at the G1/S boundary and a subsequent decrease in G2/M. These variations are obvious in primary cells. In our study, the variations observed in CAF-1 expression cannot be due to widespread genetic differences as they have been observed between asynchronously proliferating and G0 arrested cells from the same cell line (FIGS. 1B, 1C, 4) and also between Hs578T and Hs578Bst lines derived from the same mammary tissue (FIGS. 2, 4). Considering the cell cycle variations of CAF-1 RNA amounts and their downregulation upon cell cycle exit, it is tempting to speculate on a possible transcriptional regulation via Rb/E2F. Indeed, a putative E2F binding site has been found in p150 promoter by in silico studies. This does not exclude an additional regulation at the protein level, since CAF-1 p150 and p60 both comprise a PEST domain which is an amino acid sequence common to rapidly degraded proteins, potentially acting as a signal for targeting proteins for degradation by the proteasome. Furthermore, CAF-1 activity may not be regulated only by CAF-1 protein amount but also by post-translational modifications such as phosphorylation/dephosphorylation and recruitment to DNA via PCNA as described in previous studies. Indeed, it has already been shown that CAF-1 hyperphosphorylation in mitosis inhibits its chromatin assembly activity and CAF-1 phosphorylation in interphase has been associated with chromatin assembly coupled to DNA repair. In any case, the labelling at the protein level provides a reliable marker of cell proliferation.

The observations in cell line models were further explored in a physiological context by studies on tissue samples. These studies showed a direct correlation at the protein level between CAF-1 p60 and several proliferation markers. This is most likely reflecting the behavior of CAF-1 entire complex. Indeed, results from a transcriptome analysis in human breast cancer show that CAF-1 p150 belongs to the same 'proliferation cluster' as genes involved in DNA replication. Other proliferation markers, like PCNA, Ki-67 and MCM proteins, have already been validated and used successfully in different tumoral types. However, PCNA immunoreactivity can be affected by the time of fixation and the use of Ki-67 has limitations due to (i) the lack of knowledge concerning its role in cell proliferation, (ii) the systematic requirement of an antigen retrieval step for its immunodetection. On the contrary, CAF-1 can be detected directly on cytological preparations (supplementary FIG. S6: Expression of Ki-67 and phosphorylated p60 analyzed by immunofluorescence in MCF7 cells with (+) or without (−) an antigen retrieval step as described in Material and Methods. Bar, 10 µm) and the link between CAF-1 and cell proliferation has been well documented, lying in a PCNA-mediated coupling between CAF-1 activity and DNA replication. Although CAF-1 activity is also directly coupled to DNA repair (nucleotide excision repair) and CAF-1 is recruited to chromatin upon UV irradiation, its expression is not induced upon DNA damage. Thus CAF-1 detection by immunostaining is unlikely to be due to repair events and only reflects the proliferative state. Furthermore, PCNA and Ki-67 have not proved useful in every cancer type, especially for cervical smear analysis. On the other hand, several arguments point to the use of CAF-1 as a general marker in a variety of tumor types as demonstrated for breast, colon, gastric, renal, thyroid, prostate, endometrial and cervical cancers. This is consistent with the expression of CAF-1 in cells derived from a variety of tissue types (293 derived from kidney, HeLa derived from cervix, 1BR3 derived from skin and mammary cells (this work)). Interestingly, CAF-1 is conserved across species indicating a potential use of this marker in non human material (Polo S E, Cancer Research, 2004, 64:2371-2381). Regarding antibodies targeting MCM proteins, obviously they do not detect only actively proliferating cells but also cells licensed for proliferation, thus they appear to be highly sensitive markers for proliferative potential. It is proposed that their use could be complemented by the use of CAF-1, which is a more specific marker of actively proliferating cells. The combined use of these two markers could provide a powerful diagnosis tool for assessing cancer progression. Additionally, long-term follow-up studies would be of major interest to determine the relationship between CAF-1 expression and patients' outcome. Finally, all proliferation markers mentioned above have been involved in DNA replication but in addition, CAF-1 provides a direct link to the control of chromatin organization that is critical for many aspects of DNA metabolism including gene expression. This may represent a good illustration of the importance of chromatin related events in the context of cancer.

Methods and Kits for Detecting CAF-1 Marker on Cytological/histological Preparations A) Method Suited for Cryosections, Cytospined or Smeared Samples, on Coverslips or Slides Kit Content:
 F1 solution=fixative (paraformaldehyde 4% in PBS) Kept frozen at −20° C.
 CAF-1 p60 antibody: mAb8133 Abcam (kept frozen at −20° C.)
 P solution=permeabilizing solution (TritonX-100 0.2% in PBS) Kept at room temperature Additional Material Required:
 Buffer: Phosphate Buffer Saline (PBS)
 Quenching agent: Hydrogene Peroxide 30% Ph. Eur.
 Vectastain Elite ABC kit (PK-6200 or PK-6102 Abcys) containing blocking agent (horse serum), secondary antibody (anti mouse IgGs or anti-mouse and rabbit IgGs), reagents A and B to prepare the avidin-biotin complex
 Revelation system: Liquid DAB Substrate-Chromogen System (K3466, DAKO)
 Counter-staining solution: Hematoxylin solution (Papanicolaou 1a, Merck)
 Ethanol
 Toluene Rectapur for Anapath (Prolabo)
 Entellan microscopy (Merck)

Protocol: all steps are carried out at room temperature, in 4 well-plates if using samples on coverslips and in coplin-jars if using samples on slides 1. Fix the samples by incubation in F1 diluted 1:2 in PBS for 20 min
2. Wash 3 times in PBS
3. Incubate 7 min in P solution
4. Wash 3 times in PBS
5. Quench endogenous peroxidases by incubation in 0.3% Hydrogene Peroxide (diluted in MetOH 100%) for 30 min (protect from light)
6. Wash 3 times in PBS
7. Incubate in blocking solution (75 µl horse serum in 5 ml PBS) for 15 min
8. Remove the blocking solution
9. Incubate for 45 min with CAF-1 primary antibody (1:1000 in blocking solution)
10. Wash 3 times in PBS
11. Incubate for 30 min with secondary antibody (1:200 blocking solution)
12. Prepare the Avidin-Biotin complex by adding 20 µl reagent A and 20 µl reagent B in 1 ml PBS. Let stand for 30 min
13. Wash the samples 3 times in PBS
14. Incubate for 30 min with the Avidin-Biotin complex
15. Wash 3 times in PBS
16. Incubate for 10 min in the dark with peroxidase substrate (5 µl DAB in 1 ml substrate)
17. Wash in tap water for 5 min
18. Counter-stain 1 min in Hematoxylin solution (diluted 1:4 in ultra pure water and freshly filtered on 0.2 µm)
19. 1st wash in ultra pure water
20. 2nd Wash in tap water for 5 min
21. Dehydrate the samples through graded ethanol series.
22. Incubate in Toluene for 2 min
23. Mount in Entellan B) Method Suited for Paraffin-embedded Tissues Kit Content:
F2=Fixative: neutral buffered formalin 10%
R solution=Antigen retrieval buffer: 10 mM citrate buffer pH 6.1 (kept nat 4° C.)
CAF-1 p60 antibody: mAb8133 Abcam (kept frozen at −20° C.)

Additional Material Required:
Buffer: Phosphate Buffer Saline (PBS)
Quenching agent: Hydrogene Peroxide 30% Ph. Eur.
Vectastain Elite ABC kit (PK-6200 or PK-6102 Abcys) containing blocking agent (horse serum), secondary antibody (anti mouse IgGs or anti-mouse and rabbit IgGs), reagents A and B to prepare the avidin-biotin complex
Revelation system: Liquid DAB Substrate-Chromogen System (K3466, DAKO)
Counter-staining solution: Hematoxylin solution (Papanicolaou 1a, Merck)
Ethanol
Toluene Rectapur for Anapath (Prolabo)
Entellan microscopy (Merck)
microtome equipment Protocol: all steps are carried out at room temperature in coplin-jars
1. Fix tissue samples for 24 h in F2 solution.
2. Prepare 4 µm paraffin-embedded tissue sections
3. Remove paraffin and hydrate tissue sections by incubations in toluene and graded ethanol series
4. Rinse for 5 min in tap water
5. Boil tissue sections in R buffer for 15 min in the microwave, followed by 20 min cooling at room temperature
6. Wash for 5 min in ultra pure water
7. Wash for 5 min in PBS
8. Quench endogenous peroxidases by incubation in 0.3% Hydrogene Peroxide (diluted in ultra pure water) for 30 min (protect from light)
9. Wash 3 times in PBS
10. Incubate in blocking solution (75 µl horse serum in 5 ml PBS) for 15 min
11. Remove the blocking solution
12. Incubate for 1 h with CAF-1 primary antibody (1/500 in blocking solution)
13. Wash 3 times in PBS
14. Incubate for 30 min with secondary antibody (1 µl in 200 µl blocking solution)
15. Prepare the Avidin-Biotin complex by adding 20 µl reagent A and 20 µl reagent B in 1 ml PBS. Let stand for 30 min
16. Wash the samples 3 times in PBS
17. Incubate for 30 min with the Avidin-Biotin complex
18. Wash 3 times in PBS
19. Incubate for 10 min in the dark with peroxidase substrate (5 µl DAB in 1 ml substrate)
20. Wash in tap water for 5 min
21. Counter-stain by 1 min incubation in Hematoxylin solution (diluted 1:5 in distilled water and freshly filtered on 0.2 µm).
22. Wash once in ultra pure water and then in tap water for 5 min
23. Dehydrate the samples through graded ethanol series.
24. Incubate in Toluene for 2 min
25. Mount in Entellan Methods for Detecting CAF-1 Marker on RNA Extracts from Fine Needle Aspirates Kit Content:

Kit Content:
Lyophilized forward and reverse primers for CAF-1 p60 and p150 and RPLPO, the amount of provided primer (e.g. 100 nmol) being mentioned on each tube. Upon arrival, primers should be resuspended in ultrapure H2O to a final concentration of 100 µm and be kept at 20° C.

| Primer CAF-1 p60 forward: | cggacactccaccaagttct | (SEQ ID NO: 1) |
|---|---|---|
| Primer CAF-1 p60 reverse: | ccaggcgtctctgactgaat | (SEQ ID NO: 2) |
| Primer CAF-1 p150 forward: | cagcagtaccagtcccttcc | (SEQ ID NO: 5) |
| Primer CAF-1 p150 reverse: | tctttgcagtctgagcttgttc | (SEQ ID NO: 6) |
| Primer RPLPO forward: | ggcgacctggaagtccaact | (SEQ ID NO: 7) |
| Primer RPLPO reverse: | ccatcagcaccacagccttc | (SEQ ID NO: 8) |

Control: Vials of cDNA made from RNA extracts of cycling and quiescent primary cells, which can be used to set up experimental conditions.

Additional Material Required:

RNA extracts:
 Trizol (Invitrogen)
 Chloroform
 Isopropyl alcohol
 Ethanol

Reverse transcription:
 Superscript II reverse transcriptase (Invitrogen)
 Random primers (Invitrogen)
 dNTP solution
 RnaseIN (Promega) or RNaseOUT (Invitrogen)

Q-PCR:
 Lightcycler 2.0 System (Roche)
 Lightcycler FastStart DNA Master SYBR Green I reaction kit (Roche)
 LightCycler 20 µl capillaries (Roche)
 LightCycler capillaries centrifuge adaptor (Roche)

Protocol

RNA Extracts

RNA extracts are made from collected cells using Trizol (Invitrogen), according to manufacturers instructions. The RNA extracts are kept at −80° C. and are not subjected to Dnase digestion.

Reverse Transcription

Reverse Transcription is performed using Superscript II reverse transcriptase (Invitrogen), according to manufacturers instructions, using 1 µg RNA extract and 3 µg of random primers (Invitrogen) per reaction. cDNA is kept at −80° C. and is not subjected to RNase H digestion.

Quantitative PCR

Reaction Mix:

Analysis is performed using the Lightcycler 2.0 System (Roche) and the Lightcycler FastStart DNA Master SYBR Green I reaction kit (Roche). Primers are diluted 1:10 in ultrapure H2O to obtain a 10 µM solution. cDNA is diluted 1:20 for the reactions from which expression levels will be calculated. In addition, at least three subsequent 1:4 cDNA dilutions are made in order to assess primer efficiency and amplification reliability. Per reaction is used: 2 µl of the Lightcycler hotmix, 4 µl of 25 mM MgCl2, 0.6 µl of 10 µM forward primer, 0.6 µl of 10 µM reverse primer, H2O to a final volume of 15 µl. Finally, 5 µl of cDNA is added per capillary. Capillaries are centrifuged 1 minute at 1000 rpm before entering into the Lightcycler 2.0 System.

PCR Program:

| | |
|---|---|
| Initial denaturation: | 95° C. for 15 minutes |
| 50 amplification cycles: | 95° C. for 15 seconds |
| | 60° C. for 15 seconds |
| | 72° C. for 15 seconds followed by an acquisition |
| Melting curve: | from 60° C. to 95° C. 0.1° C./second; continuous acquisition |

Analysis:

Melting curves are checked for the presence of a single amplification product. Amplification curves should display a correct sigmoid form. The efficiency of all primer pairs should be close to 2.

The crossing points (Cp) of the samples are noted. Quantity of CAF-1 p150 or p60 is normalized according to RPLPO by applying the following formula, in which E is the mean efficiency of primer pairs and in which x reflects the quantity of CAF-1 p150 or p60 mRNA relative to the quantity of RPLPO mRNA in a given sample:

$$E^{(Cp\ RPLPO - Cp\ CAF-1)} = x$$

The invention thus provides novel proliferation markers, helpful in cancer diagnosis, prognosis and in monitoring tumor response to therapies. It also opens up interesting perspectives in fundamental cancer research, especially in the comprehension of how CAF-1 expression is integrated into pathways leading to tumorigenesis.

Taken together, said data demonstrate that CAF-1 p60 and p150 subunits fulfil the criteria of a novel proliferation marker of interest for cancer diagnosis in various solid tumors (breast, colon, gastric, renal, thyroid, prostate, endometrial, cervical and breast cancers) and providing accurate predictive information regarding survival in renal cancer.

The invention claimed is:

1. A method for assessing the tumoral state of renal cells in a human or non human biological sample comprising renal cells, wherein said biological sample is suspected of comprising renal tumoral cells, said method comprising the steps of:
   a. detecting and evaluating the expression level of Chromatin Assembly Factor-1 (CAF-1) p60, p150, or p60 and p150 subunits in said biological sample and in a control sample, wherein said control sample (i) comprises healthy renal cells from the same tissue type as said biological sample; (ii) comprises renal tumoral cells from the same tissue type as said biological sample and is characterized by histological grade, or (iii) comprises renal tumoral cells taken prior to treatment from the same tumor and same patient as said biological sample;
   b. comparing the CAF-1 subunit expression level in said biological sample with that of said control sample; and
   c. correlating (i) a higher CAF-1 subunit expression level in said biological sample as compared to that of said control sample with a higher proliferative state of the renal cells in said biological sample as compared to that of the renal cells in said control sample, or (ii) a lower CAF-1 subunit expression level in said biological sample as compared to that of said control sample with a lower proliferative state of the renal cells in said biological sample as compared to that of the renal cells in said control sample.

2. The method of claim 1, wherein the detection is carried out at the protein level.

3. The method of claim 2, wherein the detection is carried out on phosphorylated CAF-1 p60 subunit.

4. The method of claim 2, wherein the detection is carried out on the total cellular fraction or the chromatin-bound fraction of said CAF-1 subunits, or on the phosphorylated CAF-1 p60 subunit in the cell nucleus.

5. The method of claim 2, wherein the detection is performed by immunofluorescence, Western blot, protein chips, immunocytochemistry or immunohistochemistry.

6. The method of claim 5, wherein said detection involves the use of anti-CAF-1 antibodies, or antibodies targeted against said individual CAF-1 subunits or against fragments thereof, said antibodies being polyclonal or monoclonal antibodies.

7. The method of claim 1, wherein said control sample comprises healthy renal cells from the same tissue type of tissue as said biological sample, and wherein a higher CAF-1 subunit expression level in said biological sample as compared to that of said control sample is correlated with the presence of tumor cells in said biological sample.

8. The method of claim 1, wherein said control sample comprises renal tumoral cells from the same tissue type as said biological sample and is characterized by histological grade, and wherein a higher CAF-1 subunit expression level in said biological sample as compared to that of said control sample is correlated with a higher histological grade in said biological sample as compared to that of said control sample.

9. The method of claim 1, wherein said biological sample comprises renal tumoral cells taken from the renal tumor of a patient after treatment, wherein said control sample comprises renal tumoral cells taken prior to treatment from the same renal tumor and same patient as said biological sample, and wherein a lower CAF-1 subunit expression level in said biological sample as compared to that of said control sample is correlated with an acceptable efficiency of treatment for the patient.

10. The method of claim 1, further comprising detection of Ki-67 or PCNA or MCM or combinations thereof.

11. The method of claim 1, wherein assessing cellular proliferation based on CAF-1 p60, p150, or p60 and p150 subunit expression level is performed by standard Western blot, immunocytochemical and/or immunohistochemical procedures using CAF-1 specific antibodies on cell extracts, fixed cells or tissue sections from a solid renal tumor.

12. The method of claim 1, comprising using a kit for assessing the tumoral state of the renal cells in the human or non human biological sample suspected of comprising renal tumoral cells, said kit comprising a fixative solution for the cell sample to be tested and anti-CAF-1 p60 and/or CAF-1 p150 antibody.

13. The method of claim 12, wherein the kit further comprises a buffer, a blocking agent, a secondary antibody, reagents to prepare an avidin-biotin complex and/or a counter-staining solution.

14. The method of claim 12, wherein the kit further comprises coverslips or slides.

15. A method for assessing the survival prognostic of a patient with renal cancer comprising the steps of:
 a. detecting and evaluating the expression level of Chromatin Assembly Factor-1 (CAF-1) p60, p150, or p60 and p150 subunits in a human or non human biological sample suspected of comprising renal tumoral cells;
 b. comparing the CAF-1 subunit expression level in said biological sample with that of a cut off value; and
 c. correlating a CAF-1 subunit expression level in said biological sample below said cut off value with a higher patient survival prognostic.

* * * * *